(12) United States Patent
Lin

(10) Patent No.: US 8,795,376 B2
(45) Date of Patent: Aug. 5, 2014

(54) POSITIONING INSERT FOR INTERVERTEBRAL DISC DISORDER

(71) Applicant: A-Spine Asia Co., Ltd., Taipei (TW)

(72) Inventor: Jin-Fu Lin, Taipei County (TW)

(73) Assignee: A-Spine Asia Co., Ltd., Taipei (TW)

( * ) Notice: Subject to any disclaimer, the term of this patent is extended or adjusted under 35 U.S.C. 154(b) by 153 days.

(21) Appl. No.: 13/677,205

(22) Filed: Nov. 14, 2012

(65) Prior Publication Data

US 2013/0073048 A1   Mar. 21, 2013

Related U.S. Application Data

(63) Continuation-in-part of application No. 12/168,874, filed on Jul. 7, 2008, now abandoned.

(51) Int. Cl.
*A61F 2/44* (2006.01)
*A61B 17/70* (2006.01)
*A61F 2/30* (2006.01)

(52) U.S. Cl.
CPC ......... *A61F 2/44* (2013.01); *A61F 2002/30848* (2013.01); *A61F 2002/30281* (2013.01); *A61F 2002/30899* (2013.01); *A61F 2002/30777* (2013.01); *A61F 2002/30576* (2013.01); *A61F 2002/30507* (2013.01); *A61F 2002/30785* (2013.01); *A61B 17/7059* (2013.01); *A61F 2002/30884* (2013.01); *A61F 2002/30594* (2013.01); *A61F 2002/30904* (2013.01); *A61F 2310/00023* (2013.01); *A61F 2002/30604* (2013.01); *A61F 2/4465* (2013.01)
USPC ....................................... 623/17.16

(58) Field of Classification Search
USPC ........................... 623/17.11–17.16
See application file for complete search history.

(56) References Cited

U.S. PATENT DOCUMENTS 5,591,235 A * 1/1997 Kuslich ................. 606/261

* cited by examiner

*Primary Examiner* — Sameh Boles
(74) *Attorney, Agent, or Firm* — Chun-Ming Shih

(57) ABSTRACT

A positioning insert for two adjacent vertebral bodies includes a plate like insert adapted to fix relative positions of the two adjacent vertebral bodies and provided with a sharp edge oppositely formed relative to the dull side and first holes defined through a side face of the plate like insert, wherein the sharp edge is formed to have an angle between 5 to 15 degrees; and an annular insert adapted to be inserted into a space between the two adjacent vertebral bodies and having second holes and a slot defined in a peripheral side face thereof to accommodate the plate like insert so as to have the plate like insert received in the slot.

9 Claims, 9 Drawing Sheets creating a space in spinal disc for fittingly receiving an annular insert inserting the annular insert into the space fixing a plate like insert in the annular insert directly

POSITIONING INSERT FOR INTERVERTEBRAL DISC DISORDER

CROSS-REFERENCE TO RELATED APPLICATIONS

This application is a continuation-in-part (CIP) of application Ser. No. 12/168,874 filed on Jul. 7, 2008 now abandoned by Jin-Fu LIN, the same inventor of this application and the content thereof is hereinafter taken for reference and incorporated.

FIELD OF THE INVENTION

The present invention relates to a positioning insert, and more particularly, to a positioning insert for intervertebral disk disorders, which is implanted between intervertebral space to relieve the pain from the deficiency of the intervertebral disk.

BACKGROUND OF THE INVENTION

Spinal interbody fusion is a commonly performed procedure for degenerative disorders. A spinal fixation device is usually used to control intervertebral movement, and at present the spinal fixation devices generally use bone screws as the basic elements and the screws are attached to a rod or a plate outside of the spinal column to constitute a complete fixation system. The screw based fixation systems can be implanted to the spinal column from posterior, anterior or lateral side and they have been proved in biomechanical tests to be capable of controlling six-way of intervertebral movement, including axial rotation, lateral bending, and flexion and extension. Take posterior inserted bone-screw-based spinal fixation system for instance, the implantation method includes dissecting back muscles until posterior bony elements of the spinal column are exposed. Four screws are then threaded through the pedicles into two adjacent vertebral bodies, and connected two plates or rods on both sides.

Since early 1990, interbody fusion cage has been popularized until today and are used to maintain intervertebral height and to enhance fusion. The cage can be inserted from posterior, posterolateral, anterior or lateral trajectory. Bone graft is put inside the cage and fusion will occur within an expected time frame. The so-called stand-alone cage uses a fusion cage without any supplemented posterior or anterior fixation device. The biomechanical weakness of the stand-alone cage is that the cage can control flexion and lateral bending movement, but effectiveness in controlling extension and axial rotation movement is not as good as expected. Therefore, intervertebral movement is not fully under controlled by using the stand alone cage, and the fusion rate is reported suboptimal. To obtain stability which is a prerequisite for successful fusion, a supplemented screw based spinal fixation device is recommended.

Based on the understanding of this screw based spinal fixation device, US patent application No. 2004/0034353A1 filed on Aug. 11, 2003 discusses an apparatus and method for anterior spinal stabilization. This application requires a pre-installed rivet or screw to undergo the entire implantation process, which is complicated and too time consuming. This process is not applicable for patient suffered from Osteoporosis for the implantation process destroys the vertebral body too much.

Another US patent application No. 2005/0021029A1, filed on Jul. 25, 2003 discusses an annulus repair system, instruments and techniques. This application is aimed for damaged intervertebral disc such that almost the materials involved in the process is related to non-rigid material, which is not able to withstand the twist, bend and rotation of the spine.

Still another US patent application No. 2004/0220670A1 filed on Feb. 6, 2004 involved an articular disc prosthesis and method for treating spondylolisthesis. In this application, there is a raised plate-like segment aimed for sliding movement of the intervertebral body after the insert is implanted. This structure does have the function to prevent intervertebral movement in sideways and twist. The movement prevention function still cannot prevent bending movement of the intervertebral body. Another US patent application No. 2005/0159813A1 filed on Jan. 15, 2004 involves a spinal implant construct and method for implantation. It is not applicable for patient suffered from Osteoporosis for the implantation process destroys the vertebral body too much.

U.S. Pat. No. 5,591,235 filed on Mar. 15, 1995 involves an annular and hollow column extending all the way through the intervertebral body, which destructs too much of the intervertebral body. A rod intended to be fitted into the slot in the hollow column is narrow and provides no space for new bone growth. In addition, the edge of the rod is blunt and it cannot extend into the intervertebral body directly. A previously defined slot has to be ready before the use of the rod, which is too complex and complicated. U.S. Pat. No. 6,558,424, filed on Jun. 28, 2001 provides a modular anatomic fusion device involves a wedged block for insertion into the intervertebral space and the rough surface formed on the top and bottom faces of the wedged block is to increase friction with the vertebral body. With the help of the rough surface, the positioning of the modular anatomic fusion device is fixed relative to the intervertebral body. However, it still cannot withstand the twist and bending movement of the intervertebral body. In yet another US patent application No. 2003/0083746A1, a porous annular column is provided to replace the intervertebral disc. It is quite obvious that after the porous annular column is inserted between the intervertebral bodies, the spacer cannot withstand the bending, twisting or rotation of the spine.

In summary, to achieve a successful interbody fusion, screw based or non-screw based spinal fixation devices are used to control six-way of the intervertebral movement, in conjunction with a fusion cage. These fixation devices require complicated assembling procedure and may be hazardous to the human body.

SUMMARY OF THE INVENTION

The present invention improves upon known screw based spinal fixation devices, which are bulky, complicated in design and handling, for the purpose of limiting intervertebral movement. In a basic form of embodiment, the present invention relates to a plate like insert with a sharp edge and an annular insert associated with the plate like insert to be implanted into the intervertebral bodies to withstand the rotation, twisting movement of the spine. Above all, the plate like insert is to fix the intervertebral space to prevent any bending movement of the patient.

In still another objective of the present invention, the positioning insert comprises a plate like insert having a sharp edge with an angle between 5 to 15 degrees.

A different objective of the preferred embodiment of the present invention is that the plate like insert is aimed to joint two adjacent intervertebral bodies which are divided by an intervertebral space. In order to securely hold two adjacent intervertebral bodies together, a part of the plate like insert that extends into either one of the two adjacent intervertebral bodies has a height which is one fourth to three fourths (¼~¾) of the height of the intervertebral body.

In yet another objective of the preferred embodiment of the present invention is that the plate like insert extends a distance into the two adjacent intervertebral bodies, which is one fourth to half (¼~½) of the thickness of either one of the two adjacent intervertebral bodies.

DESCRIPTION OF THE PREFERRED EMBODIMENT

The above and other objectives, features and advantages of the present invention will become apparent from the following detailed description taken reference with the accompanying drawings.

Figure 1:
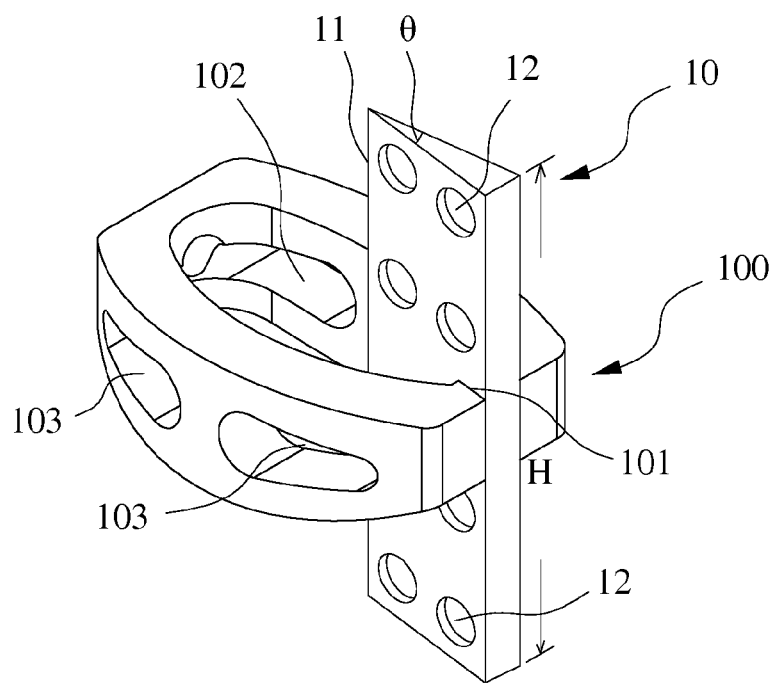
FIG. 1 is a perspective view of the positioning insert of the present invention.

The preferred embodiment of the present invention which is shown in FIG. 1 comprises a plate like insert (10) and an annular insert (100) with a vertical slot (101) defined to accommodate the plate like insert (10). The plate like insert (10) is substantially a wedge like plate, which allows one side of the plate to be a dull side and one side of the plate to be a sharp side. The surface of the plate is perforated to have first holes (12) to facilitate bone ingrowth through the first holes (12).

The annular insert (100) has a thickness substantially adapted to the thickness of the intervertebral disc so that the annular insert (100) is able to be inserted into a space between intervertebral bodies to replace the damaged intervertebral disc. The annular insert (100) has a slot (101) defined in a peripheral side face to accommodate the plate like insert (10) and second holes (103) to facilitate bone ingrowth. The plate like insert (10) and the annular insert (100) can be made of any biocompatible materials such as titanium, carbon fiber, polyether ether ketone (PEEK), and with tensile strength strong enough to resist fatigue failure. The surfaces of both the plate like insert (10) and the annular insert (100) can be serrated to increase contact area with the bones. The plate and the cage in FIG. 1 are two independent structures and they also can be manufactured into one integrated device. The plate also can be used independently with any brand of cage in the market as long as the plate and the cage are suitable in the same intervertebral space.

Figure 2:
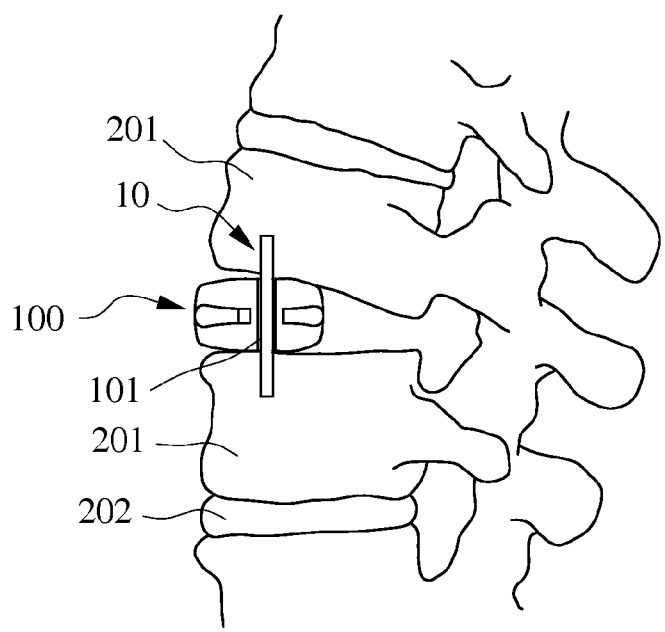
FIG. 2 is a schematic side plan view showing the application of the positioning insert of the preferred embodiment of the present invention, wherein the plate like insert is applied to join two adjacent intervertebral bodies.
Figure 3:
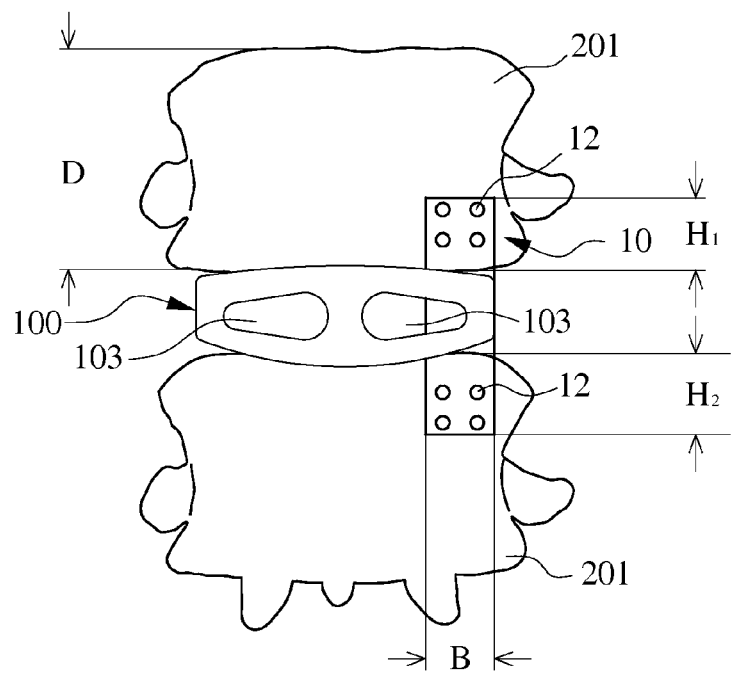
FIG. 3 is a side plan view showing how the plate like insert as well as the annular insert is applied to fix the relative position between two adjacent intervertebral bodies.

With reference to FIGS. 2 and 3, it is noted that the positioning insert constructed in accordance with the preferred embodiment of the present invention is adapted to fit into two adjacent vertebral bodies (201) with an intervertebral space (202) defined between the two adjacent vertebral bodies (201). When an intervertebral disc is damaged and the patient is suffering from severe pain due to the damaged intervertebral disc, often, the last option for the doctor to relieve the patient from pain is to proceed an operation to remove the damaged intervertebral disc and then fix the relative position between the two adjacent vertebral bodies (201).

To successfully relieve the patient from pain, the annular disk (100) is first inserted into the intervertebral space (202) after the damaged intervertebral disc is removed. After the annular insert (100) is positioned between two adjacent vertebral bodies (201), the plate like insert (10) is inserted into the two adjacent vertebral bodies (201) from the lateral side of each of the two vertebral bodies (201). The plate like insert (10) has a dull side and a sharp edge (11) opposite to the dull side. In order to facilitate the insertion of the plate like insert (10), an auxiliary tool, such as a medical use hammer, is employed on the dull side of the late like insert (10) so as to force the plate like insert (10) into the predetermined position. Also, to increase the ease of insertion of the plate like insert (10) into the two adjacent vertebral bodies (201), the sharp edge (11) of the plate like insert (10) has an acute angle between zero to fifteen (0~15), preferably five to fifteen (5~15) degrees to allow the plate like insert (10) to be inserted directly into two adjacent vertebral bodies (201). Therefore, when the plate like insert (10) is forced into the two adjacent vertebral bodies (201), the sharp edge (11) will not damage too much to the vertebral bodies (201). From numerous experiments, it is learned that if the angle of the sharp edge (11) is more than 15 degrees, the sharp edge (11) will be too dull to penetrate the vertebral column and if the angle is smaller than 5 degree, the sharp edge (11) will be too fragile to force into the vertebral bodies (201) and may be broken during the penetration.

Again, to ensure the stability of the positioning insert of the preferred embodiment of the present invention, after the plate like insert (10) is inserted into the two adjacent vertebral bodies (201), a partial height of the plate like insert (10) inserted into either one of the two adjacent vertebral bodies (201), H1 and H2 as indicated in FIG. 3, is between one fourth to two fourths (¼~²⁄₄) of the height D of either one of the two adjacent vertebral bodies (201). However, if the height D of either one of the two adjacent vertebral bodies (201) reaches one fourth to three fourths (¼~¾), it is still acceptable. Another feature of the preferred embodiment of the present invention is that after the plate like insert (10) is inserted into two adjacent vertebral bodies (201), a depth of the plate like insert (10) inserting into either one of the two vertebral bodies (201) is between one fourth to a half of a thickness of either one of the vertebral bodies (201). If the depth of the plate like insert (10) extended into the two adjacent two vertebral bodies (201) exceeds more than a half of the thickness of either one of the two adjacent vertebral bodies (201), fracture of the spinal column easily occurs during operation. However, if the depth of the plate like insert (10) extended into the two adjacent two vertebral bodies is less than a quarter (¼), the stability of the plate like insert (10) may cause a problem.

Figure 4:
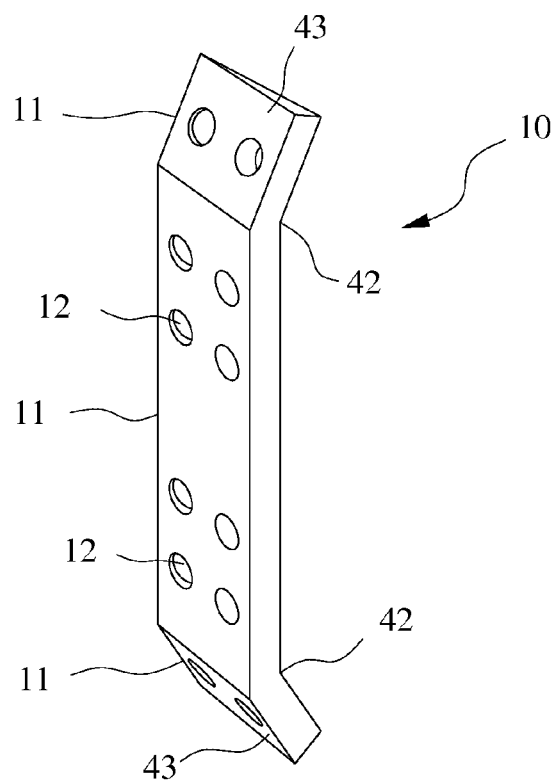
FIG. 4 is a perspective view showing a different embodiment of the plate like insert, wherein two distal ends of the plate like insert are respectively tilted to an angle to strengthen the positioning effect after being implanted to fix the two adjacent intervertebral bodies.
Figure 5:
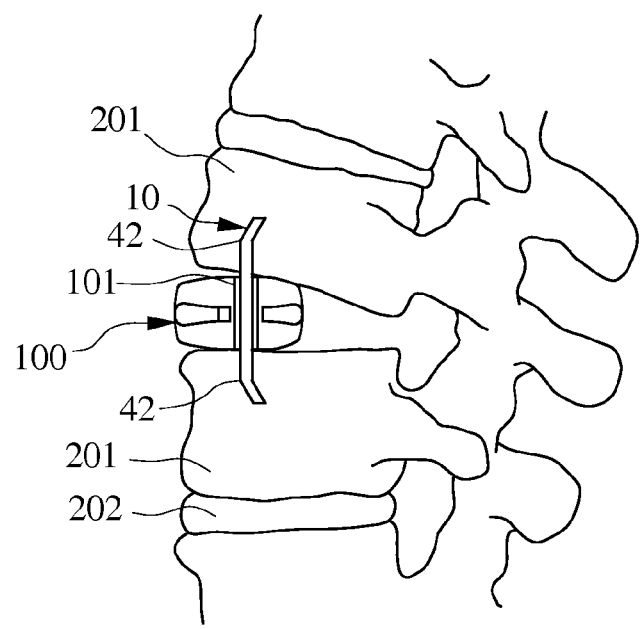
FIG. 5 is a side plan view showing the application of how the embodiment shown in FIG. 4 is applied to join two adjacent intervertebral bodies.
Figure 6:
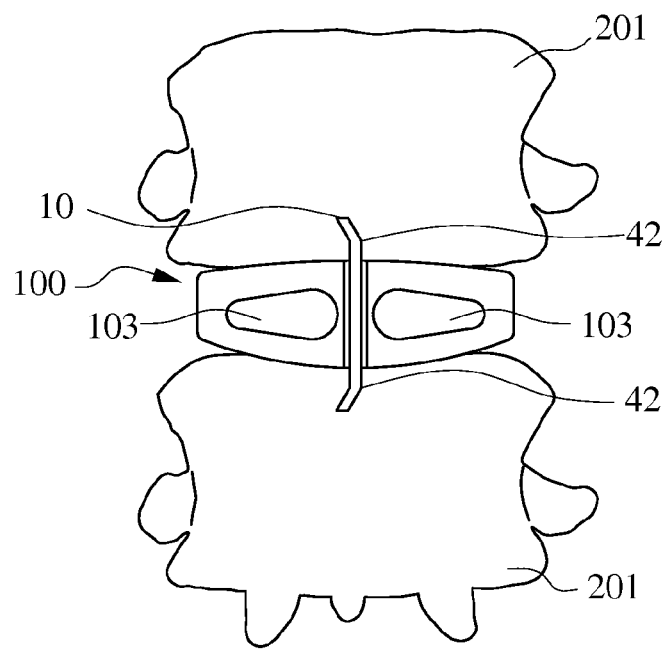
FIG. 6 shows another embodiment of the plate like insert, wherein the tilted angle is opposite to that of the embodiment shown in FIG. 5.

With reference to FIGS. 4, 5 and 6, it is noted that the plate like insert (10) now has a bent (42) formed on two a longitudinal portion thereof and a tilted portion (43) formed on two distal ends thereof such that after the plate like insert (10) is inserted into the two vertebral bodies (201), the tilted portions (43) increases the stability of the plate like insert (10) in each of the two vertebral bodies (201).

Figure 7:
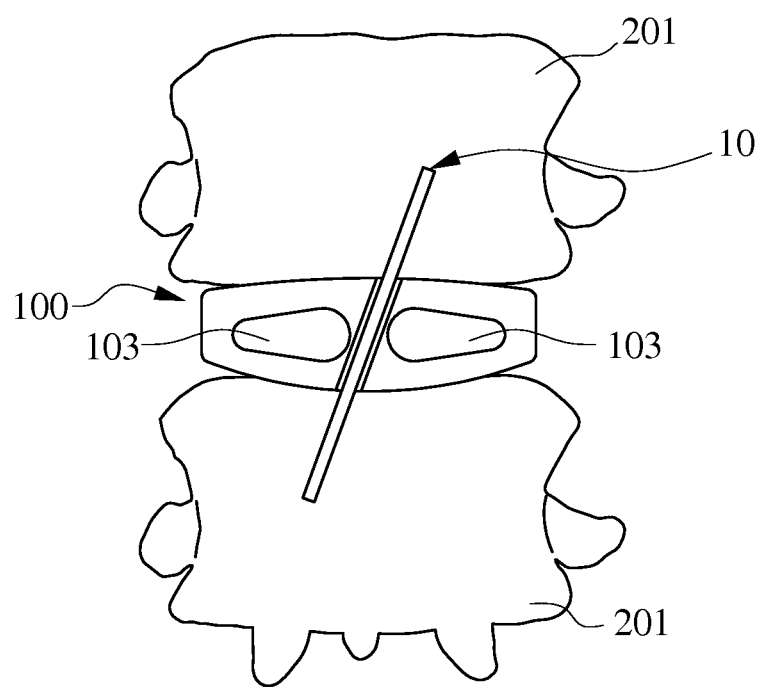
FIG. 7 is a side plan view showing still another preferred embodiment of the positioning insert of the present invention.
Figure 8:
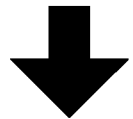
FIG. 8 is a flow chart showing steps of the method employed in the present invention.
Figure 8:
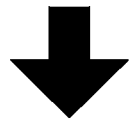
Figure 9:
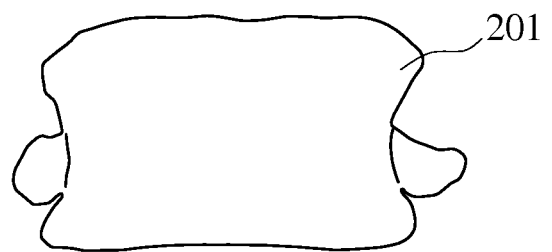
FIG. 9 is a schematic view showing the step of creating a space in spinal disc for fittingly receiving an annular insert.
Figure 9:
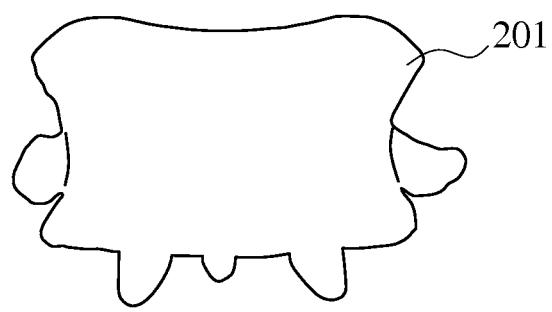
Figure 10:
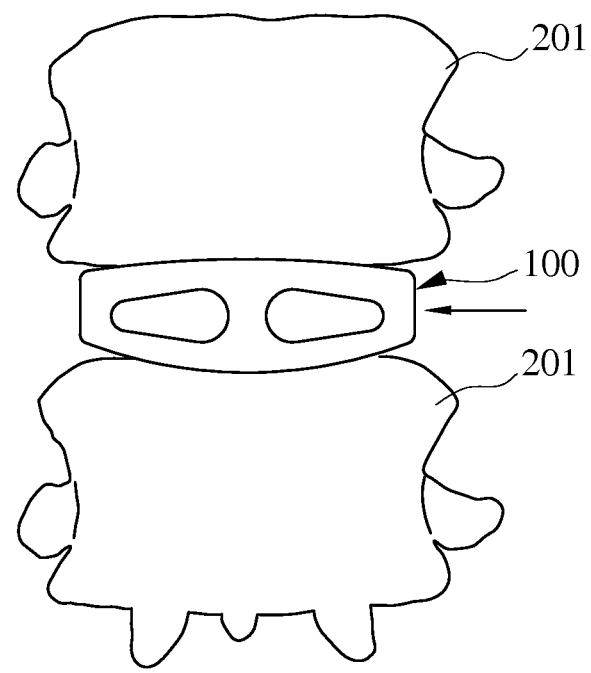
FIG. 10 is a schematic view showing the step of inserting the annular insert into the space.
Figure 11:
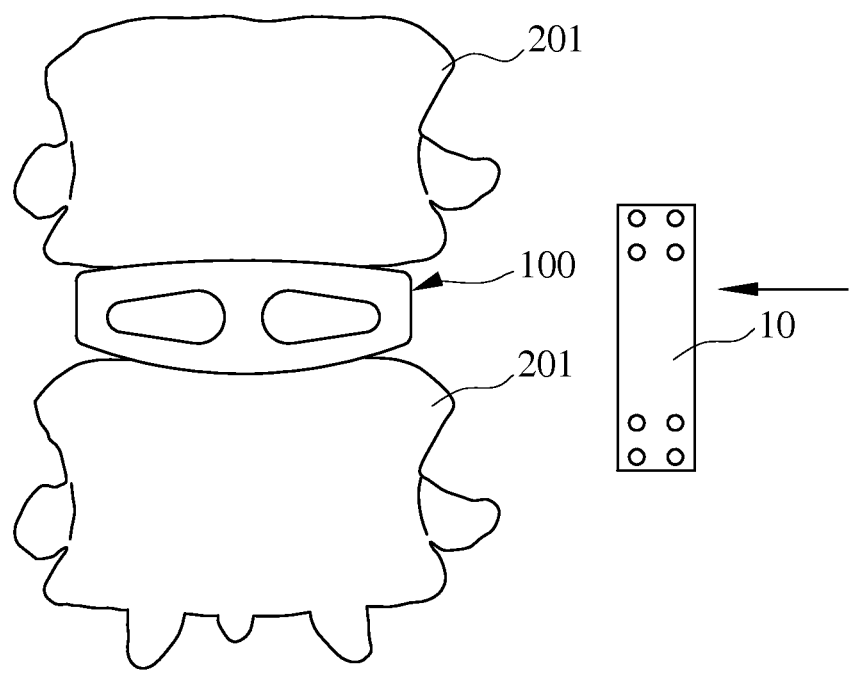
FIG. 11 is a schematic view showing the step of fixing a plate like insert in the annular insert directly.
Figure 12:
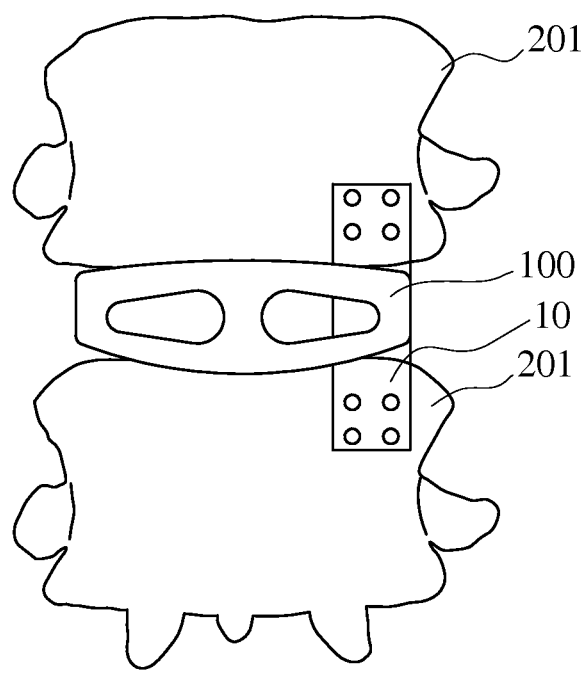
FIG. 12 is a schematic view showing the complete of the surgical operation.

FIG. 7 shows another preferred embodiment of the annular insert (100), wherein the vertical slot (101) is an oblique one such that after the plate like insert (10) is fitted into the slot (101), the plate like insert (10) is tilted relative to the annular insert (100). As a result of the oblique slot (101) in this embodiment, the stability of the positioning insert of the preferred embodiment of the present invention is now enhanced.

From the above description, with reference to FIG. 8 and FIGS. 9 to 12, a preferred embodiment of the steps of the present invention is shown, it is noted that when the positioning insert constructed in accordance with the preferred embodiments of the present invention is to be employed, a space created in spinal disc between the two adjacent vertebral bodies (201) is first defined so that the annular insert (100) is able to be fittingly received in the space. After the annular insert (100) is inserted into the space defined between the two adjacent vertebral bodies (201), the plate like insert (10) is then forced into the slot of the annular insert (100).

During the process of inserting the positioning insert of the preferred embodiment of the present invention, the annular insert (100) and the plate like insert (10) are directly fixed respectively in the space between the two adjacent vertebral bodies (201) and in the slot of the annular insert (100), no extra operation procedure is needed. As a result, risks of any complications, bleeding or damage to the body is greatly reduced. In order to have the best performance and the best effect after installing the positioning insert of the preferred embodiment of the present invention, it is noted that the positioning insert is used in the thoracic vertebral and the lumbar vertebral.

It is noteworthy to point out that the aforementioned preferred embodiments are used for illustrating the present invention only, but not intended to limit the scope of the present invention. Those skilled in the art can make modifications such as changing the shape of the plate like insert (10), the bent (42) of the plate like insert (10), the first holes (12); and the annular insert (100) with a slot (101) to accommodate the plate like insert (10). The aforementioned and other equivalent modifications are intended to be covered by the scope of the present invention.

In summation of the above description, the plate like insert (10), and the annular insert (100) with the slot (101) for the plate of the present invention herein achieve the same purpose of three-dimensional fixation of current bone screw based fixation system and without bulky design, complicated assembling procedure and minimize the possible hazards to the human body, further complies with the patent application requirements, and thus is duly filed for patent application.

While the invention has been described by means of specific embodiments, numerous modifications and variations could be made thereto by those skilled in the art without departing from the scope and spirit of the invention set forth in the claims.

What is claimed is:

1. A positioning insert for two adjacent vertebral bodies respectively having a height, a thickness and a intervertebral disc between the two adjacent vertebral bodies, the positioning insert consisting essentially of: a plate like insert adapted to fix relative positions of the two adjacent vertebral bodies and provided with a wedge shape to have a dull side, a sharp edge oppositely formed relative to the dull side and first holes defined through a side face of the plate like insert, wherein the sharp edge is formed to have an angle between 5 to 15 degrees; and an annular insert adapted to be inserted into a space between the two adjacent vertebral bodies and having second holes and a slot defined in a peripheral side face thereof to accommodate the plate like insert so as to have the plate like insert received in the slot, wherein the plate like insert has a bent and a tilted portion extending from the bent, and wherein the slot is oblique such that after the plate like insert is accommodated in the slot, the plate like insert is tilted relative to the annular insert.

2. The positioning insert as claimed in claim 1, wherein a partial height of the plate like insert inserted into either one of the two adjacent vertebral bodies is between ¼~¾ of the height of either one of the two adjacent vertebral bodies.

3. The positioning insert as claimed in claim 2, wherein a depth of the plate like insert inserted into either one of the two vertebral bodies is between one fourth to a half of the thickness of either one of the vertebral bodies.

4. The positioning insert as claimed in claim 2, wherein the plate like insert has a bent and a tilted portion extending from the bent.

5. The positioning insert as claimed in claim 2, wherein the slot is oblique such that after the plate like insert is accommodated in the slot, the plate like insert is tilted relative to the annular insert.

6. The positioning insert as claimed in claim 1, wherein a depth of the plate like insert inserted into either one of the two vertebral bodies is between one fourth to a half of the thickness of either one of the vertebral bodies.

7. The positioning insert as claimed in claim 6, wherein the plate like insert has a bent and a tilted portion extending from the bent.

8. The positioning insert as claimed in claim 6, wherein the slot is oblique such that after the plate like insert is accommodated in the slot, the plate like insert is tilted relative to the annular insert.

9. The positioning insert as claimed in claim 1, wherein the slot is oblique such that after the plate like insert is accommodated in the slot, the plate like insert is tilted relative to the annular insert.

\* \* \* \* \*